United States Patent [19]
Wheeler

[11] Patent Number: 5,919,168
[45] Date of Patent: Jul. 6, 1999

[54] INJECTION NEEDLE PROTECTION

[76] Inventor: Alton D. Wheeler, 3940 Fox Meadow La., Pasadena, Tex. 77504

[21] Appl. No.: 08/918,241

[22] Filed: Aug. 25, 1997

[51] Int. Cl.⁶ ..................................................... A61M 5/32
[52] U.S. Cl. ........................................... 604/198; 604/263
[58] Field of Search ..................................... 604/198, 272, 604/192, 263, 110

[56]           References Cited

U.S. PATENT DOCUMENTS

| | | |
|---|---|---|
| 5,334,149 | 8/1994 | Nortman et al. . |
| 5,334,151 | 8/1994 | Santilli . |
| 5,334,155 | 8/1994 | Sobel . |
| 5,334,187 | 8/1994 | Fischell et al. . |
| 5,336,176 | 8/1994 | Yoon . |
| 5,336,177 | 8/1994 | Marcus . |
| 5,336,187 | 8/1994 | Terry et al. . |
| 5,336,191 | 8/1994 | Davis et al. . |
| 5,336,197 | 8/1994 | Kuracina et al. . |
| 5,336,198 | 8/1994 | Silver et al. . |
| 5,336,199 | 8/1994 | Castillo et al. . |
| 5,336,200 | 8/1994 | Streck et al. . |
| 5,336,201 | 8/1994 | von der Decken . |
| 5,338,303 | 8/1994 | King et al. . |
| 5,338,304 | 8/1994 | Adams . |
| 5,338,306 | 8/1994 | Srivatsa . |
| 5,338,310 | 8/1994 | Lewandowski . |
| 5,338,311 | 8/1994 | Mahurkar . |
| 5,342,308 | 8/1994 | Boschetti . |
| 5,342,309 | 8/1994 | Hausser . |
| 5,342,310 | 8/1994 | Ueyama et al. . |
| 5,342,320 | 8/1994 | Cameron . |
| 5,342,322 | 8/1994 | Nathan et al. . |
| 5,342,323 | 8/1994 | Haining . |

*Primary Examiner*—Wynn Wood Coggins
*Assistant Examiner*—Sharon Finkel
*Attorney, Agent, or Firm*—William W. Haefliger

[57]           ABSTRACT

An injection-type needle unit and injection needle protector that comprises an injection needle unit body; an injection needle carried by the body and having a tip to penetrate flesh; a tip protector carried by the needle to move between a relatively retracted position spaced from the tip, and a relatively extended position shielding the tip; and restrictor structure carried by the body to prevent relative displacement of the protector from extended position to a position that would expose the tip.

8 Claims, 4 Drawing Sheets

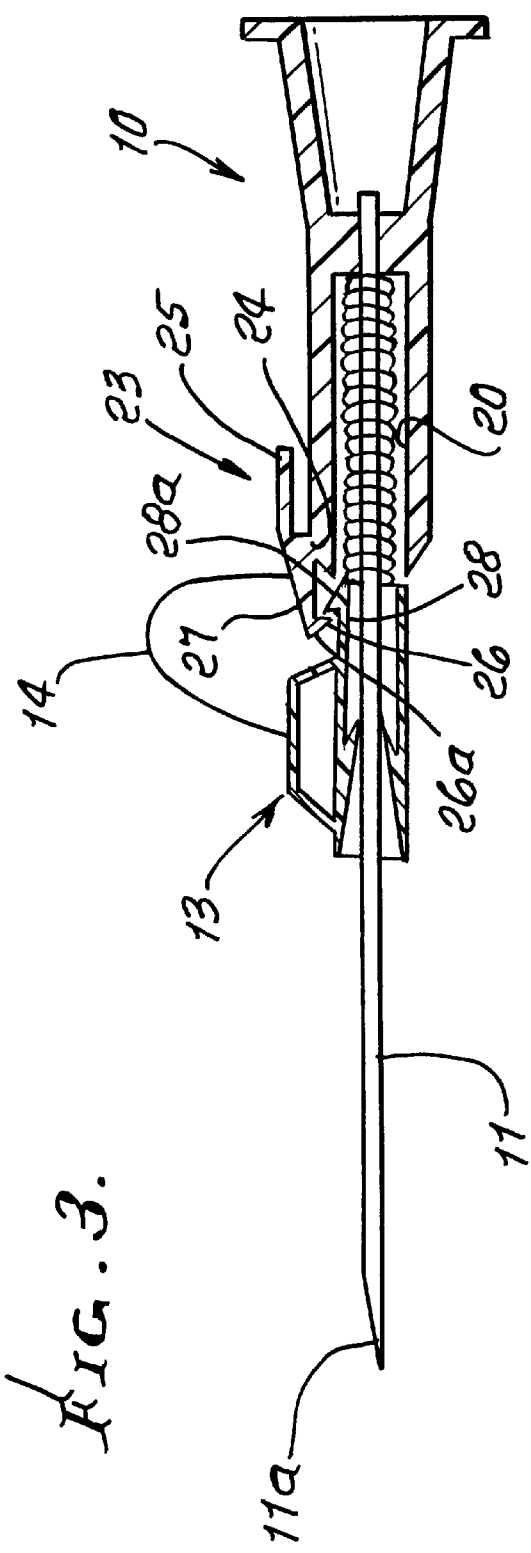
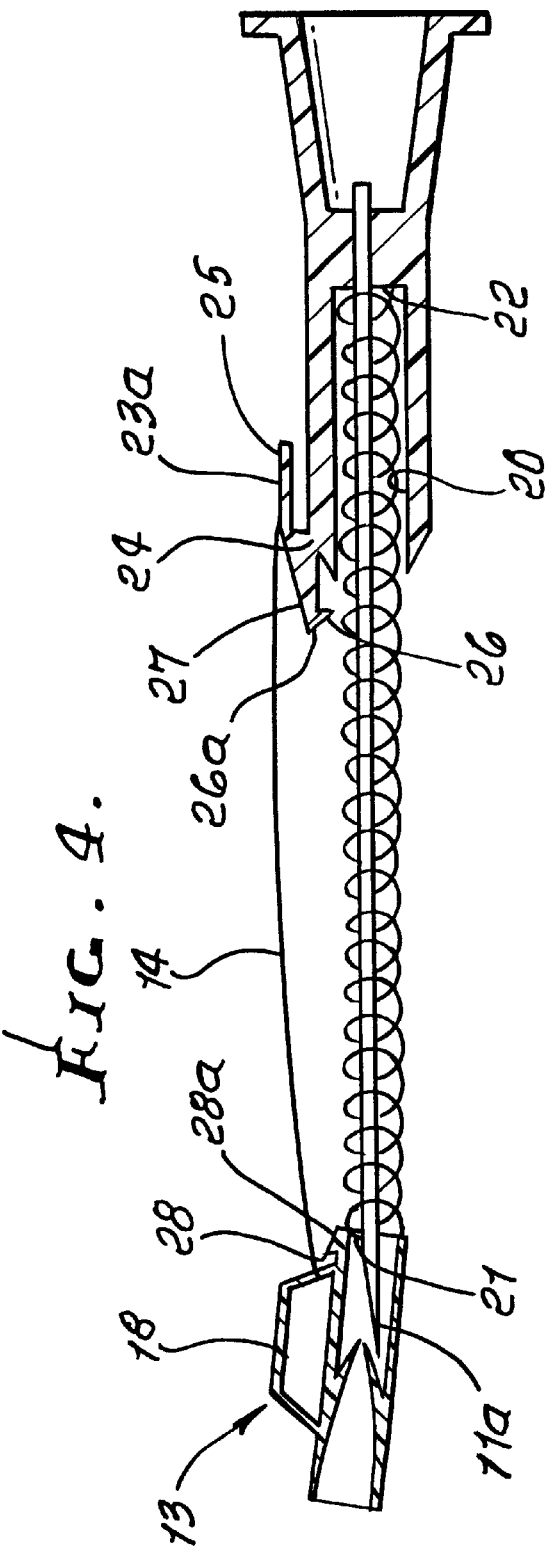

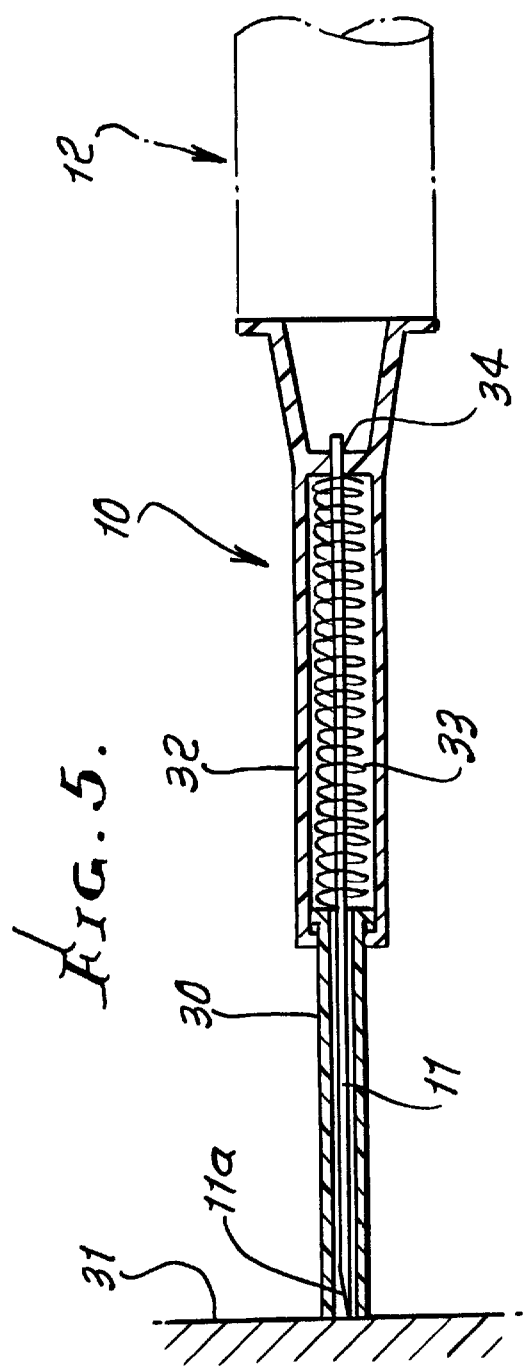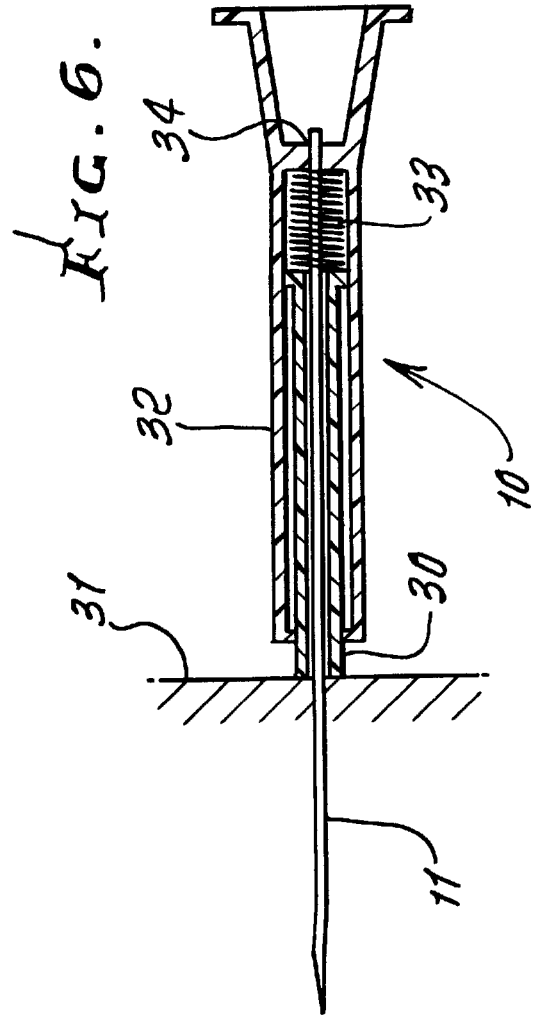

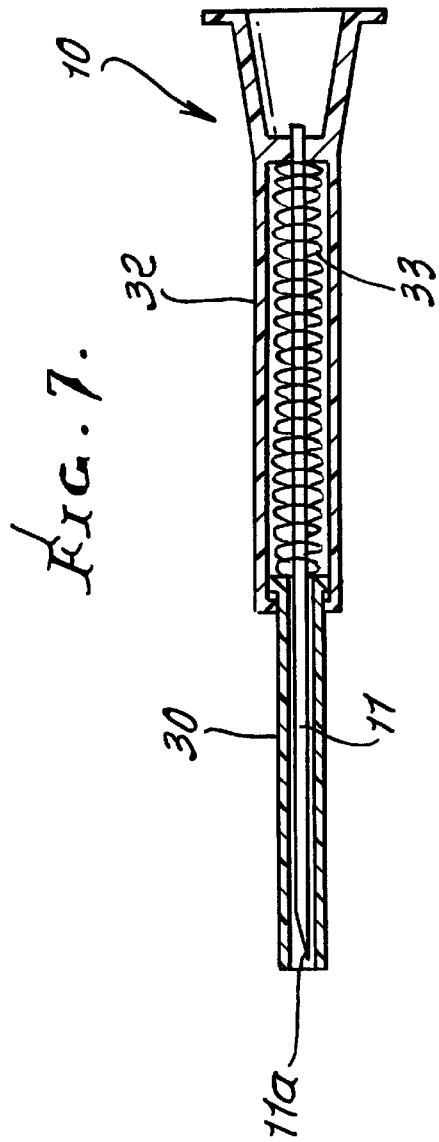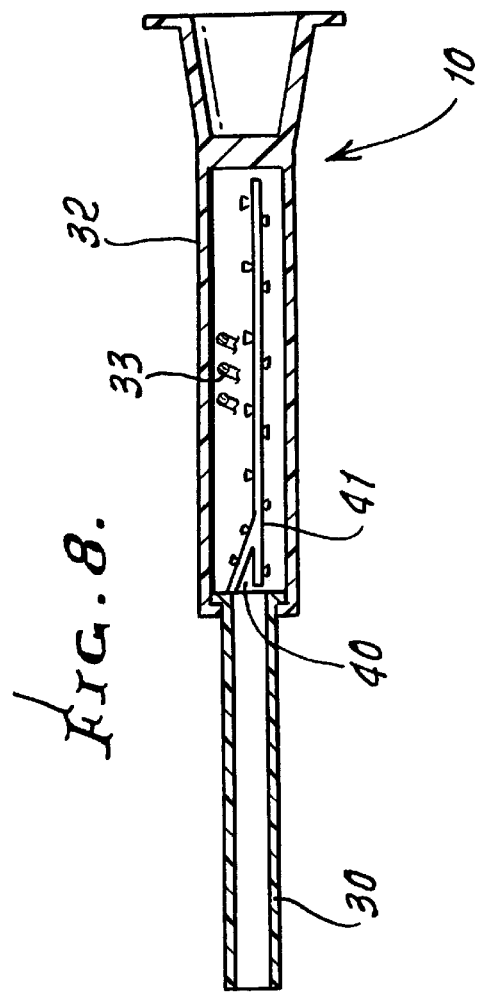

INJECTION NEEDLE PROTECTION

BACKGROUND OF THE INVENTION

This invention relates generally to protection of injection needles against unwanted penetration of human body parts, such as hands and fingers; and more particularly, to covering or shielding of needle tips after their use.

There is continual need for simple, effective and low-cost reliable means to shield syringe needle tips, as after usage, in order to prevent spread of infection. This need is acute, as when medical staff must inject fluid substances into, or withdraw blood, from patients who may well be HIV carriers, or carriers of hepatitis-related substances, or other contaminants.

Prior devices and methods, of which I am aware, lack the unusual advantages in construction, modes of operation and results, as are now enabled by the present invention.

SUMMARY OF THE INVENTION

It is a major object of the invention to provide improved protection methods and means meeting the above need. Basically, the apparatus of the invention is associated with an injection-type needle unit and injection needle, which may be attached to a syringe, and comprising:

a) an injection needle unit body,
b) an injection needle carried by the body and having a tip to penetrate flesh,
c) a tip protector carried by the needle to move between a relatively retracted position spaced from the tip, and a relatively extended position shielding the tip,
d) and a restrictor or restrictor means carried by the body to prevent relative displacement of the protector from its extended position to a position that would undesirably expose the tip.

In one form of the invention, the restrictor comprises a simple, flexible lanyard integrally connected to the tip protector and to the needle unit body; and in another form of the invention, the restrictor comprises blocking means for blocking relative displacement of the protector from extended position toward retracted position.

It is another object of the invention to provide a protector that has an interior pocket into which the needle tip is received and shielded when the protector is in extended position. The protector may have an interior flap adjacent the pocket, to trap the needle tip, as will be seen. In this regard, the flap and protector may both be generally tubular, the needle extending through the flap and protector as the protector slides along the needle between retracted and extended position. Accordingly, the needle itself acts as a guide for such sliding; and the flap may have conical form, as will appear.

Yet, another object is to provide yieldable means biasing the protector directionally along the needle. Such yieldable means may typically comprise a coil spring having coils extending about the needle. The spring is compressed when the protector is in retracted position; and a holder is provided for holding the protector in retracted position, and which is releasable to allow such yieldable means to urge the protector toward the needle tip, into shielding position.

A further object is to provide a protector comprising a tube extending about the needle and receivable in a bore in the body in protector-retracted position.

An additional object is to provide such a needle unit that is endwise connectible or connected to a syringe body remotely from the needle tip protector, to accommodate flow of fluid between the needle and the syringe body or barrel (i.e., human body fluid flow into the syringe, via the needle, or fluid medicament from the syringe into the flesh, via the needle, as during injection).

These and other objects and advantages of the invention, as well as the details of an illustrative embodiment, will be more fully understood from the following specification and drawings, in which:

DRAWING DESCRIPTION

FIG. 3 is a view like FIG. 1 but showing a modified device having yieldable means to urge the protector toward the needle tip;

FIG. 4 is like FIG. 3 but showing the spring released and the protector displaced to cover and protect the needle tip;

FIG. 5 is a view like FIG. 4 but showing a modified protector in the form of a sleeve, in extended position;

FIG. 6 is a view like FIG. 5 but showing the protector sleeve in retracted position, as during injection;

FIG. 7 is a view like FIG. 6 but showing the sleeve in extended position after injection; and FIG. 8 is a view like FIG. 7 and showing addition of a blocking means to hold the sleeve in extended, needle covering, position, after completion of injection.

DETAILED DESCRIPTION

Figure 1:
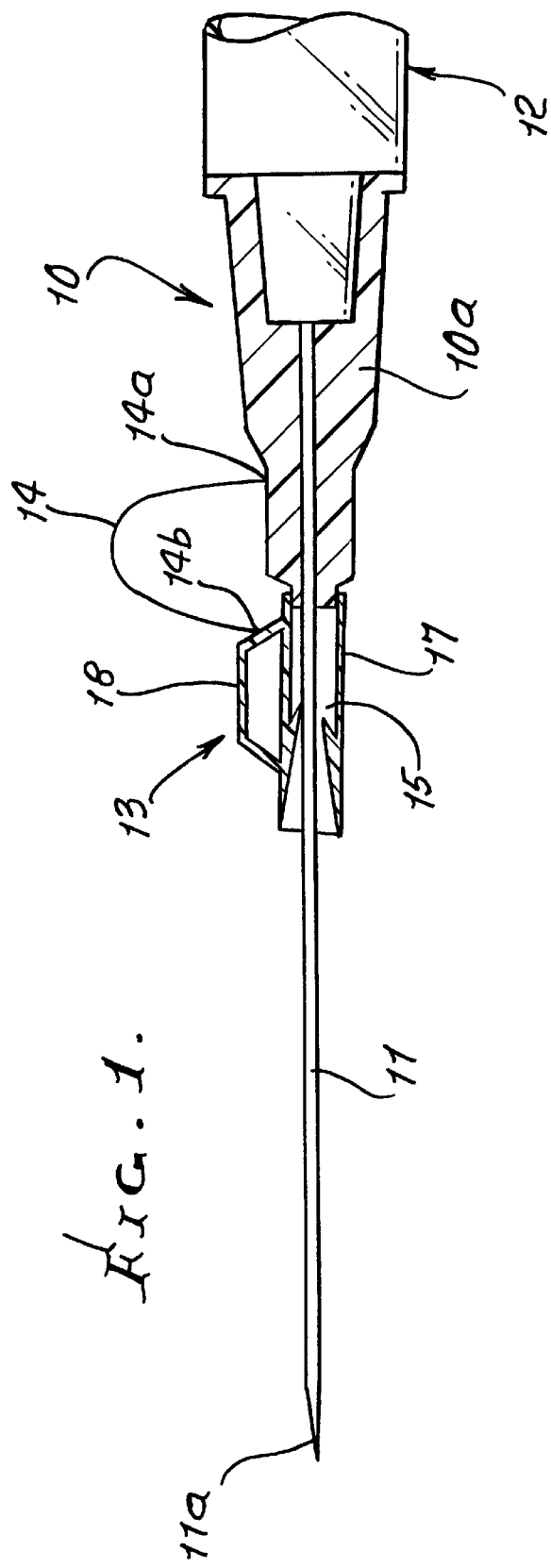
FIG. 1 is a side elevational view of one preferred form of apparatus incorporating the invention, showing a needle tip protector in retracted position.
Figure 2:
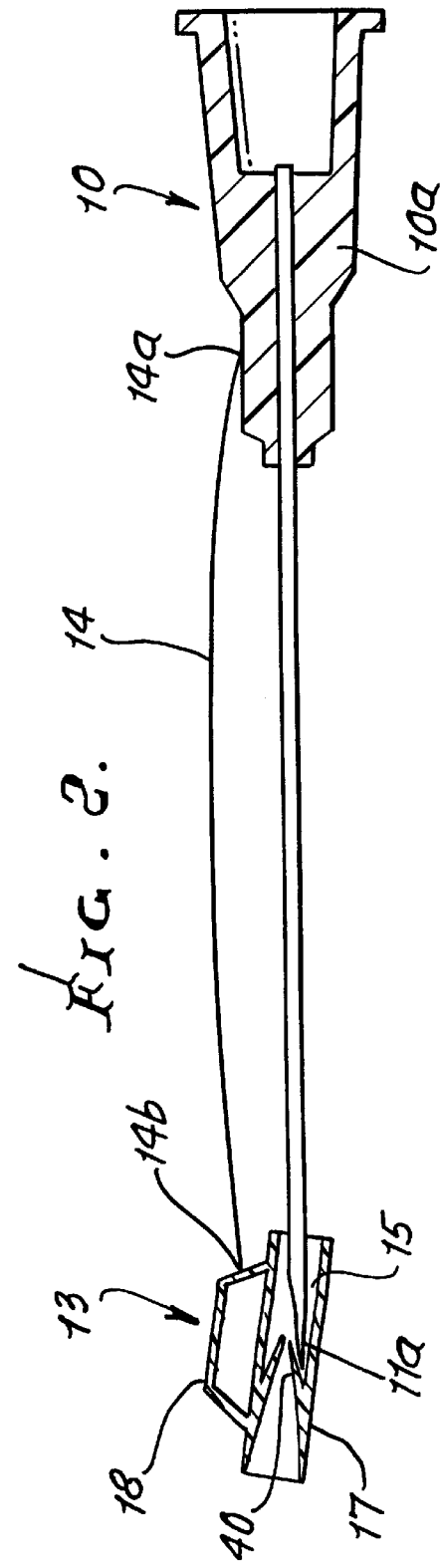
FIG. 2 is like FIG. 1 but showing the protector in extended position, covering the needle tip.

Referring to FIGS. 1 and 2, an injection needle unit 10 carries an elongated needle 11, which is tubular, for fluid-passing purposes. A syringe, indicated at 12, is suitably removably endwise attached to the unit 10 for passing fluid between the syringe barrel and the needle. The needle has a sharp tip, indicated at 11a, to penetrate flesh.

In accordance with one preferred form of the invention, a needle tip protector is carried by the needle to slide thereon between a relatively retracted position, spaced from the tip, and a relatively extended position, shielding or encompassing the tip. See, for sample, the protector indicated generally at 13, supported in retracted position in FIG. 1, and advanced to extended position in FIG. 2.

Restrictor means, as for example is indicated at 14, is carried by the needle unit body and serves to prevent relative displacement of the protector off the needle, i.e., from extended position, seen in FIG. 2, to a position that would expose or free the needle tip to penetrate flesh, for example after its use, in which case the needle tip might be contaminated. In the form of the invention seen in FIGS. 1 and 2, the restrictor means advantageously comprises a flexible lanyard—one end 14a of which is connected to the body, and the other end 14b of which is connected to the protector.

The lanyard may consist of molded plastic material, and may be integrally molded with a needle unit body 10a, also made of plastic, and/or the protector 13, also made of plastic. Accordingly, in FIG. 1 the lanyard has looping, retracted position; and in FIG. 2, it is stretched out generally linearly to hold the protector against removal from the needle tip. The lanyard may be similar to clothing hang-tag lanyards, as are known.

In the specific form illustrated, the protector has an interior pocket 15 into which the needle tip is received when the protector is in extended position, as shown in FIG. 2. To this end, the protector may have an interior flap 40 adjacent the pocket, and spaced from the tubular side wall 17 of the protector to form therewith the pocket 15. As shown, the flap has conical configuration, tapering rearwardly toward the unit 10, to diverge away from side wall 17. The needle extends through a reduced opening formed by the frusto-conical flap, so that the protector is guided on and along the needle, as it is manually advanced to extended position seen in FIG. 2. At that point, the needle tip rides out of the conical flap and can only enter the annularly extending pocket 15 to entrap the tip within the protector preventing unwanted penetration of flesh, such as pricking the fingers or hands of the user. It will be noted that the protector has a sidewardly raised button 18, which is easily manually displaced from FIG. 1 to FIG. 2 positions. Manual manipulation of the protector easily assures needle tip apture into the pocket 15.

The form of the invention shown in FIGS. 3 and 4 is in many respects the same as of FIGS. 1 and 2, the same identifying numerals being used, where applicable. Note, however, that means is provided to bias the protector directly leftwardly and forwardly along the needle, to FIG. 4 extended position, wherein the protector traps the needle tip. Such yieldable mean is shown in the form of a coil spring received within a bore 20 in the unit 10 to forcibly act against the protector. When the protector is released from retracted position, the coil spring forcibly expands along the needle to displace the protector to FIG. 4 position. Note the coils of the spring extended about the needle. Shoulder 21 on the protector is engaged by the leftwardmost coil of the spring; and a shoulder 22 of the unit 10 is engaged by the rightwardmost coil of the spring.

Protector release means provided on holder 23 is manually operable to release the protector from connection to the body of 10, after needle use. Such release means may take the form of a lever 23a hinge connected at 24 to the body, as by plastic molding, to provide a fulcrum. When the rightward end 25 of the lever is depressed, a hook 26 on the leftward end 27 of the lever releases from a tang 28 on the protector tube, to allow the protector to be displaced to FIG. 4 position. Restoration of the protector to FIG. 3 retained position is facilitated by camming engagement of the cam surfaces 26a on the hook, and 28a on the tang.

In FIGS. 5 and 6, the construction is generally the same as in FIGS. 3 and 4, excepting that the protector 30 is shown as tubular, closely surrounding the needle. At the completion of needle use to penetrate flesh 31, the needle protrudes from the sleeve-like protector 30, as seen in FIG. 6. The protector 30 has been retracted into the body 32 of the unit 10, compressing a coil spring 33. Thereafter, when the needle is withdrawn from the flesh, as by retraction of unit 10, to which the needle is attached at 34, the protector sleeve 30 is distended from the body 32 by expansion of the spring, whereby the needle is effectively relatively retracted into the protector, as seen in FIG. 7. This prevents accidental needle tip penetration of the user's skin.

In FIG. 8, the structure is like that of FIGS. 5 through 7. However, a blocking means is added to block displacement of the protector 30 from extended position toward retracted position within a tubular body 32. Such blocking means comprises a pocket 40 within a part 41 contained within the body 32. The pocket becomes aligned with the rightward end of the wall of the protector 30 in extended position of the protector side, thereby to block rightward displacement of the protector, i.e., retraction into the tubular body 32.

I claim:

1. An injection-type needle unit and injection needle protector comprising, in combination a) an injection needle unit body, b) an injection needle carried by said body and having a tip to penetrate flesh, the needle extending forwardly, c) a tip protector carried by the needle to move between a relatively retracted position spaced from said tip, and a relatively extended position shielding said tip, d) restrictor means carried by said body to prevent relative displacement of said protector from said extended position to a position that would expose said tip, e) said protector having an interior pocket into which said needle tip is received when the protector is in said extended position, f) said protector having an interior flap adjacent said pocket, said flap being substantially conical and tapering rearwardly to form a reduced opening to guide protector movement along the needle, said pocket extending annularly about said flap and reduced opening, g) and yieldable means biasing said protector directionally along the needle, wherein said yieldable means is compressed when said protector is in said retracted position, there being a holder holding said protector in said retracted position, and which is releasable to allow said yieldable means to urge the protector toward the needle tip, said holder comprising a lever having a hinge connection to the body.

2. The combination of claim 1 wherein said restrictor means comprises a flexible lanyard.

3. The combination of claim 2 wherein said protector and lanyard are unitary and consist of molded plastic material.

4. The combination of claim 1 wherein said lanyard and at least one of the following are unitary and consist of molded plastic material:

i) said body ii) said body and said protector.

5. The combination of claim 1 wherein said body has a connection thereon to attach to the syringe body.

6. The combination of claim 1 including a syringe body endwise connected to said needle unit body to accommodate flow of fluid between said needle and said syringe body.

7. The combination of claim 1 wherein said yieldable means comprises a coil spring having coils extending about the needle.

8. The combination of claim 1 wherein said body has a bore into which said yieldable means is at least partially received in said protector retracted position.

* * * * *